United States Patent [19]
Leder et al.

[11] Patent Number: 5,474,981
[45] Date of Patent: Dec. 12, 1995

[54] USE OF THE CYTOKINE IP-10 AS AN ANTI-TUMOR AGENT

[75] Inventors: Philip Leder, Chestnut Hill; Andrew Luster, Wellesley, both of Mass.

[73] Assignee: President and Fellows of Harvard College, Cambridge, Mass.

[21] Appl. No.: 217,016

[22] Filed: Mar. 23, 1994

Related U.S. Application Data

[63] Continuation of Ser. No. 935,587, Aug. 26, 1992, abandoned.

[51] Int. Cl.⁶ .......................... A61K 38/16; A61K 38/17; A61K 38/18; C07K 14/475
[52] U.S. Cl. ................. 514/12; 514/2; 514/908; 530/350; 530/351
[58] Field of Search ................. 514/2, 12, 908; 530/324, 350, 351

[56] References Cited

PUBLICATIONS

Friedman, L. M. (editor) et al., *Fundamentals of Clinical Trials*, 2nd Edition, 1985, Mosby Yearbook, St. Louis, Mo., pp. 33–50.
Luster, A. D. et al., *J. Cell. Biochem. Suppl.*, 17 Part B: 121, 1993.
Leder, P. et al., *J. Exp. Med.*, 178(3):1057–1065, 1993.
Narumi, S. et al., *J. Leukoc. Biol.*, 52(1):27–33, 1992.
Dewald, B. et al., *Immunol. Lett.*, 32(1):81–84, 1992.
Smaller, B. R. et al., *J. Am. Acad. Dermatol.*, 25(4):627–31, 1991.
Ohmori, Y. et al., *Biochem. Biophys. Res. Comm.*, 168 (3):1261–67, 1990.
Luster, A. d. et al., *J. Exp. Med.*, 166:1084–1097, 1987.
Baggiolini et al., J. Clin. Invest. 84:1045–1049, 1989.
Gottlieb et al., J. Exp. Med. 168:941–948, 1988.
Kaplan et al., J. Exp. Med. 168:1811–1824, 1988.
Kaplan et al., J. Exp. Med. 166:1098–1108, 1987.
Luster et al., Nature 315:672–676, 1985.
Luster and Ravetch, Molecular and Cellular Biology 7:3723–3731, 1987.
Luster et al., Proc. Natl. Acad. Sci. USA 84:2868–2871, 1987.
Matsushima et al., J. Exp. Med. 169:1485–1490, 1989.
Richmond and Thomas, J. Cell. Physiology 129:375–384, 1986.
Rollins and Sunday, Molecular and Cellular Biology 11:3125–3131, 1991.
Tepper et al., Cell 57:503–512, 1989.
Wolpe and Cerami, FASEB J. 3:2565–2573, 1989.

*Primary Examiner*—Marianne P. Allen
*Attorney, Agent, or Firm*—Fish & Richardson

[57] ABSTRACT

Methods and therapeutic compositions for treating neoplasms by administration of the polypeptide IP-10, or a suitable DNA vector encoding the polypeptide IP-10.

5 Claims, 2 Drawing Sheets

```
CATCCCGAGC CAACCTTCCG GAAGCCTCCC CATCAGCACC ATG AAC CCA AGT GCT        55
                                            Met Asn Pro Ser Ala
                                             1               5

GCC GTC ATT TTC TGC CTC ATC CTG CTG GGT CTG AGT GGG ACT CAA GGG       103
Ala Val Ile Phe Cys Leu Ile Leu Leu Gly Leu Ser Gly Thr Gln Gly
                10                      15                  20

ATC CCT CTC GCA AGG ACG GTC CGC TGC AAC TGC ATC CAT ATC GAT GAC       151
Ile Pro Leu Ala Arg Thr Val Arg Cys Asn Cys Ile His Ile Asp Asp
                25                      30                  35

GGG CCA GTG AGA ATG AGG GCC ATA GGG AAG CTT GAA ATC ATC CCT GCG       199
Gly Pro Val Arg Met Arg Ala Ile Gly Lys Leu Glu Ile Ile Pro Ala
        40                  45                  50

AGC CTA TCC TGC TGC CCA CGT GTT GAG ATC ATT GCC ACG ATG AAA AAG AAT   247
Ser Leu Ser Cys Cys Pro Arg Val Glu Ile Ile Ala Thr Met Lys Lys Asn
        55                  60                  65

GAT GAG CAG AGA TGT CTG AAT CCG GAA TCT AAG ACC ATC AAG AAT TTA       295
Asp Glu Gln Arg Cys Leu Asn Pro Glu Ser Lys Thr Ile Lys Asn Leu
70                  75                  80                  85

ATG AAA GCG TTT AGC CAA AAA AGG TCT AAA AGG GCT CCT TAACTGGAGA        344
Met Lys Ala Phe Ser Gln Lys Arg Ser Lys Arg Ala Pro
                90                  95

GAAGCCACGC ACACACC                                                    361
```

FIG. 1

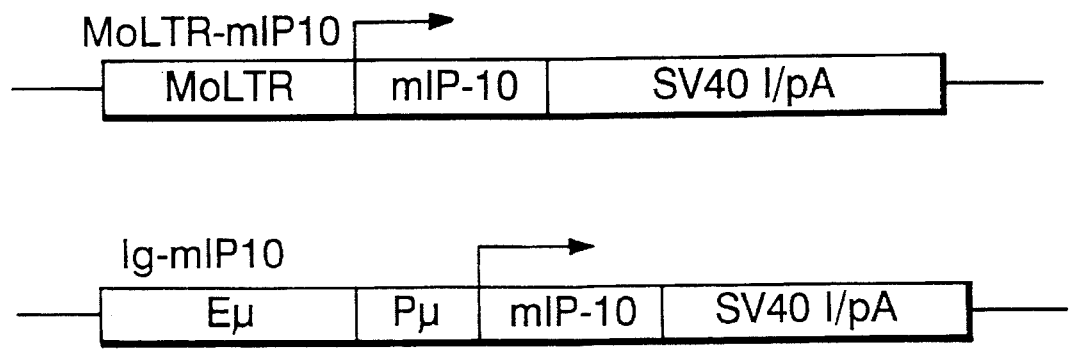
FIG. 2
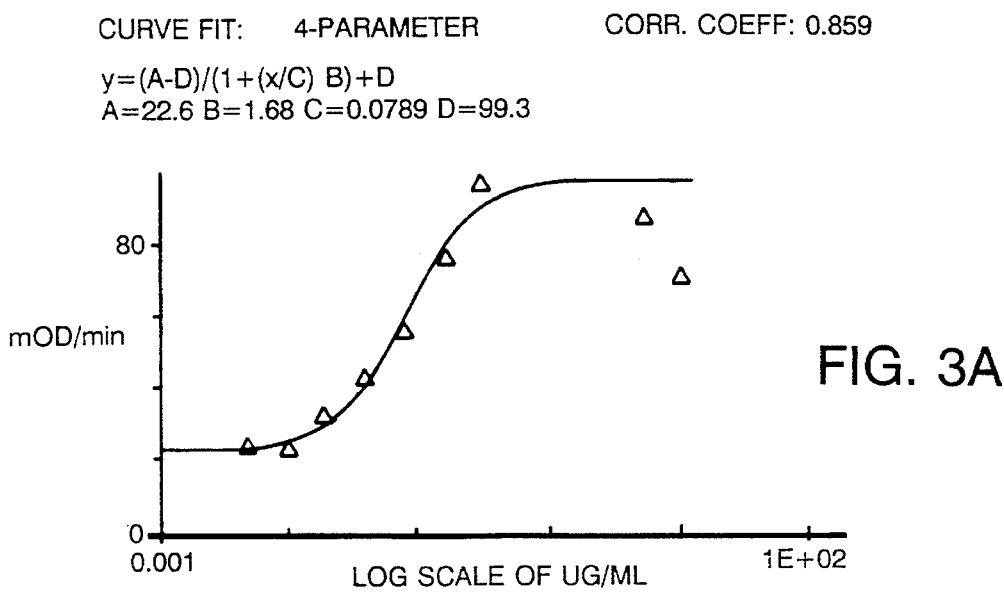
FIG. 3A
| CELL LINE | mOD/min | Conc ng./ml |
|---|---|---|
| J558l transfected with | | |
| None | 3.54+0.1 | ----- |
| MoLTR-IP-10 | 29.03+0.5 | ~20 |
| Ig-IP10 | 24.31+1.4 | ~20 |
| | | |
| K485 transfected with | | |
| None | 4.40+0.4 | ----- |
| MpLTR-IP10 | 30.35+1.7 | ~20 |
FIG. 3B

USE OF THE CYTOKINE IP-10 AS AN ANTI-TUMOR AGENT

This is a continuation of application Ser. No, 07/935,587, filed Aug. 26, 1992, now abandoned.

BACKGROUND OF THE INVENTION

The invention relates to a therapy for neoplasms which involves administration of the cytokine IP-10.

Recent studies of inflammation, growth control, and cell transformation have resulted in the definition of a novel superfamily of early response cytokines having homology to platelet factor 4 (PF4). These cytokines have immunomodulatory and growth regulatory properties. Expression of these proteins (to date at least ten different peptides have been identified) is induced in a wide variety of cell types by diverse inflammatory and mitogenic stimuli. The biological function of this burgeoning family of related proteins remains, however, largely unknown.

PF4 and βB-thromboglobulin (βTG) were the first members of this family to be identified. They are alpha-granule platelet proteins that are released together during the platelet release-reaction. Both proteins are mediators of platelet effects in inflammatory and wound healing processes. PF4 is chemotactic for neutrophils and monocytes and has been shown to inhibit angiogenesis by preventing endothelial cell proliferation in response to growth factors. ββTG modulates connective tissue elements; it is chemotactic for fibroblasts, and an unprocessed form of βTG containing four additional N-terminal amino acids is mitogenic for synovial cells and fibroblasts (reviewed in Wolpe, S.D. et al., The FASEB Journal 3: 2565–2573 (1989)).

Previously, IP-10 was isolated as the predominant mRNA induced by gamma-interferon (IFNγ) in human monocytes (Luster, A. et al., Nature 315:672 (1985)). IFNγ is a glycoprotein secreted by activated T cells which, in addition to its antiviral properties, is a potent activator of the cellular immune response. IFNγ activates macrophages, increases fibroblast and endothelial cell resistance to many non-viral pathogens, and modulates cell-surface proteins central to immune cell regulation. IP-10 (so named for induced protein of 10 kd) encodes a previously undescribed protein with approximately 30% amino acid identity to platelet factor 4 and interleukin 8 (Luster, A. D. et al., Nature 315:672 (1985)). IP-10 is secreted from a variety of cells in culture (keratinocytes, endothelial cells, monocytes and fibroblasts) in response to IFNγ (Kaplan, G. et al., J. Exp. Med. 166:1098–1108 (1987)). In addition, IP-10 is expressed in vivo during the development of a cutaneous cellular immune response by keratinocytes, endothelial cells and infiltrating dermal mononuclear cells (Gottlieb, A. B. et al., J. Exp. Med. 167: 941–948 (1988)). IP-10 expression is seen in the epidermis and dermis in the cutaneous lesions of psoriasis (Gottlieb, A. B. et al., J. Exp. Med. 167:941–948 (1988)) and tuberculoid leprosy (Kaplan, G. et al., J. Exp. Med. 167:941–948 (1988)). The homology of IP-10 to chemotactic and mitogenic proteins suggests that it may play a role in the directed migration, activation and proliferation of both local and blood-borne cells that characterize the inflammatory response.

The similarities of the intron-exon structure of PF4 and IP-10 (Luster, A. D. et al., Mol. Cell. Biol. 7: 3723–3731 (1987)) and the fact that both genes map to the long arm of chromosome 4 (Luster, A. D. et al., Proc. Natl. Acad. Sci. U.S.A. 84:2868–2871 (1986)) support the hypothesis that they evolved from a common ancestral gene by gene duplication. A remarkable number of new members of this family have recently been identified by studies that have isolated genes induced by various mitogenic or inflammatory stimuli or through the amino acid sequencing of secreted proteins in the media of activated cells (Wolpe, S. D. et al., The FASEB Journal 3:2565–2573 (1989)). A comparison of the amino acid sequences reveals that the homology between the eight human proteins ranges from approximately 20% to 70%.

These cytokines have an overlapping, yet distinct, set of ascribed functions which include chemotaxis, mitogenesis, tumoricidal activity and cell activation. For example, neutrophil activating peptide, recently named interleukin (IL)-8, is secreted from monocytes, lymphocytes and endothelial cells stimulated by IL-2, tumor necrosis factor (TNF) and lipopolysaccharide (LPS) (Baggiolini, M. et al., J. Clin. Invest. 84:1045–1049 (1989)). IL-8 is a potent chemoattractant for neutrophils and lymphocytes, it induces the respiratory burst and granule exocytosis of neutrophils, and, depending on its form, it either promotes or inhibits neutrophil adherence to endothelial cells (Baggiolini, M. et al., J. Clin. Invest. 84:1045–1049 (1989)). Monocyte hemotactic peptide (MCP), however, is released from monocytes stimulated with IL-1, LPS and granulocyte-macrophage colony stimulating factor (GM-CSF) and from fibroblasts stimulated with platelet-derived growth factor (PDGF). MCP is only chemotactic for monocytes, and can augment the tumoricidal activity of human monocytes for several human tumor lines (Matsushima, K. et al., J. Exp. Med. 169:1485–1490 (1989)). Furthermore, melanoma growth stimulatory activity, another member of this family that maps to the long arm of chromosome 4, is a known growth factor for melanoma cells and is induced in fibroblasts by PDGF and endothelial cells by IL-1, TNF and LPS (Richmond, A. et al., J. Cell. Physiol. 129:375–384 (1986)).

Several years ago an assay was developed which allows one to screen a variety of secreted proteins to test their effects on tumor growth in vivo (Tepper, R. I. et al., Cell 57: 503–512 ( 1989 ) ).

Summary of the Invention

The invention provides a method for inhibiting a neoplasm in a mammal by administering to the mammal a tumor inhibiting amount of IP-10. IP-10 may be administered according to the invention by means of DNA which encodes the polypeptide, or the polypeptide may be administered directly. Preferably, the method is used for the treatment of a leukemia or lymphoma, most preferably a leukemia or lymphoma of the immune system.

Another preferred use of IP-10 is in the treatment of a carcinoma, e.g., mammary adenocarcinoma.

Another aspect of the invention is a pharmaceutical or veterinary formulation comprising IP-10 formulated for pharmaceutical or veterinary use, respectively, optionally together with an acceptable diluent, carrier or excipient and/or in unit dosage form. In using the factors of the invention, conventional pharmaceutical or veterinary practice may be employed to provide suitable formulations or compositions.

The IP-10 may also be administered by the transplantation into the patient of host cells expressing the DNA of the instant invention or by the use of surgical implants which release the formulations of the invention.

Other features and advantages of the invention will be apparent from the following description and from the claims.

DETAILED DESCRIPTION

The drawings will first be briefly described. Drawings FIG. 1 is the DNA and amino acid sequence of the murine IP-10 gene.

FIG. 2 depicts the expression vectors MoLTR-mIP10 and Ig-mIP10.

FIG. 3(a) and FIG. 3(b) depict the expression and secretion of IP-10 by a stably transfected J558L plasmacytoma cell line and a stably transfected K495 mammary adenocarcinoma cell line. FIG. 3(a) depicts the ELISA assay standard curve on purified recombinant IP-10 produced in E. coli. FIG. 3(b) provides the quantitation of IP-10 produced by the J558L and K485 transfected cell lines.

I. IP-10 POLYPEPTIDES

The invention includes administration of any protein which is substantially homologous to IP-10 from humans or mice (FIG. 1, SEQ ID NO 1), as well as other naturally occurring IP-10. Also included in the administration of allelic variations; natural mutants; induced mutants; proteins encoded by DNA that hybridizes under high or low (e.g., washing at 2× SSC at 40° C. with a probe length of at least 40 nucleotides) stringency conditions to a nucleic acid naturally occurring (for other definitions of high and low stringency see Current Protocols in Molecular Biology, John Wiley & Sons, New York, 1989, 6.3.1–6.3.6, hereby incorporated by reference); and polypeptides or proteins specifically bound by antisera to IP-10, especially by antisera to the active site or binding domain of IP-10. The invention also includes the use of chimeric polypeptides that include IP-10.

As used herein, homologous refers to the sequence similarity between two polypeptide molecules or between two nucleic acid molecules. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions shared by the two sequences. For example, 6 of 10, of the positions in two sequences are matched or homologous then the two sequences are 60% homologous. By way of example, the DNA sequences ATTGCC and TATGGC share 50% homology.

A "substantially pure preparation" of a polypeptide is a preparation which is substantially free of the proteins with which the polypeptide naturally occurs in a cell.

The invention also includes the use of any biologically active fragment or analog of IP-10. By "biologically active" is meant possessing any in vivo or in vitro activity which is characteristic of the 98-amino acid IP-10 shown in FIG. 1 (SEQ ID NO:1). Because IP-10 exhibits a range of physiological properties and because such properties may be attributable to different portions of the IP-10 molecule, a useful IP-10 fragment or IP-10 analog is one which exhibits a biological activity in any biological assay for IP-10 activity, for example, those assays described in sections (2) and (3) of the Experimental Methods, below, and in Example 1. Most preferably, a useful fragment or analog possesses 10%, preferably 40%, or at least 90% of the activity of IP-10 (shown in FIG. 1; SEQ ID NO:1), in any in vivo or in vitro IP-10 assay.

Preferred analogs include IP-10 (or biologically active fragments thereof) whose sequences differ from the wild-type sequence only by conservative amino acid substitutions, for example, substitution of one amino acid for another with similar characteristics (e.g., valine for glycine, arginine for lysine, etc.) or by one or more non-conservative amino acid substitutions, deletions, or insertions which do not abolish the polypeptide's biological activity.

Other useful modifications include those which increase peptide stability; such analogs may contain, for example, one or more non-peptide bonds (which replace the peptide bonds) or D-amino acids in the peptide sequence.

Analogs can differ from naturally occurring IP-10 in amino acid sequence or can be modified in ways that do not involve sequence, or both. Analogs of the invention will generally exhibit at least 60%, more preferably 68%, more preferably 80%, and most preferably 95% or even 99%, homology with a segment of 20 amino acid residues, preferably more than 40 amino acid residues, or more preferably the entire sequence of a naturally occurring IP10 sequence.

Alterations in primary sequence include genetic variants, both natural and induced. Also included are analogs that include residues other than naturally occurring L-amino acids, e.g., D-amino acids or non-naturally occurring or synthetic amino acids, e.g., β or γ amino acids. Alternatively, increased stability may be conferred by cyclizing the peptide molecule.

By exposing the polypeptide to phosphorylation-altering enzymes, e.g., kinases or phosphatases modifications include in vivo or in vitro chemical derivatization of polypeptides, e.g., acetylation, methylation, phosphorylation, carboxylation, or glycosylation; glycosylation can be modified, e.g., by modifying the glycosylation patterns of a polypeptide during its synthesis and processing or in further processing steps, e.g., by exposing the polypeptide to glycosylation affecting enzymes derived from cells that normally provide such processing, e.g., mammalian glycosylation enzymes; phosphorylation can be modified by exposing the polypeptide to phosphorylation-altering enzymes, e.g., kinases or phosphatases.

In addition to substantially full-length polypeptides, the invention also includes biologically active fragments of the polypeptides. As used herein, the term "fragment" as applied to a polypeptide, will typically be at least about 40 residues, preferably at least about 60 residues in length. Fragments of IP-10 can be generated by methods known to those skilled in the art. The ability of a candidate fragment to exhibit a biological activity of IP-10 can be assessed by methods known to those skilled in the art and as described herein. Also included are IP-10 polypeptides containing residues that are not required for biological activity of the peptide such as residues that are not required for the biological activity of the polypeptide, or that result from alternative mRNA splicing or alternative protein processing events.

II. EXPERIMENTAL METHODS

1. DNA Constructions.

The murine (m) IP-10 cDNA was cloned from the murine macrophage cell line RAW264.7. RNA was isolated from RAW264.7 cells that were treated for four hours with recombinant murine gamma-interferon. This RNA was then used as template for first strand cDNA synthesis. The complete mIP-10 coding sequence was cloned from this cDNA using Taq DNA polymerase, standard PCR conditions, a 5' sense oligonucleotide AAGCGCTTCATC-CACCG (SEQ ID No. 2) and a 3' antisense oligonucleotide GCGTGGCTTCTCTCCAG (SEQ ID No. 3) based on sequences 1–17 and 362–379, respectively, from the published sequence of mIP-10 (Vanguri, P. et al., J. Biol. Chem. 265:15049–15057 (1990). The PCR product was purified by agarose gel electrophoresis, blunt-ended with klenow, kinased with T4 polynucleotide kinase, followed by blunt-end cloned into the Xho 1 site of pIgTE/N and the Eco R1 site of a MoLTR-SV40 I/pA-pBluescript expression vectors. Both expression vectors were assembled using standard cloning procedures (Sambrook et al., Molecular Cloning: A Laboratory Manual., Cold Spring Harbor Laboratory Press, Cold Spring Harbor, N.Y. (1989)) and the vectors correspond to Clone notebook numbers C-219 and C-248, respectively. Briefly, the immunoglobulin control sequences used in the generation of the plasmid pIgTE/N were derived from the plasmid pBSEμPμ which contains a 0.6 kb Ncol fragment of the human immunoglobulin heavy chain promotor derived from the plasmid Pμ (Danner and Leder, Proc. Natl. Acad. Sci. USA 82:8658–8662, 1985) and a 1.0 kb Xba1 fragment of the mouse immunoglobulin heavy chain enhancer derived from the plasmid pTARY (Banerji et al., Cell 33:729–740, 1983), placed 5' of the immunoglobulin promotor at the unique Xba1 site in pBluescript (Stategene). Both vectors contain an SV40 intron and splice and plyadenylation signals (Seed, B., Nature 329:840–842 (1987)) following the cDNA cloning site. The MoLTR was isolated as a 0.6 kb Cla1-Xma1 fragment of pZip-NeoSV(X)-1 plasmid (Cepko et al., Cell 37:1053–1062, 1984), which includes the 3' LTR of the Moloney murine leukemia virus.

2. Cell Culture and Transfection

J558L is a heavy-chain-loss variant of the BALB/c plasmacytoma line J558 (Oi, V. T. et al., Proc. Natl. Acad. Sci. USA 80:825–829 (1983)). The K485 mammary adenocarcinoma line was derived from a tumor in a transgenic mouse carrying an activated c-myc oncogene (Leder, A. et al., Cell 45:485–495 (1986)). The J558L cell line was grown in RPMI 1640 medium supplemented with 10% fetal bovine serum, 50 U/ml penicillin, 50 μg/ml streptomycin, 2 mM L-glutamine, and 57 μM 2-mercaptoethanol. K485 and RAW 264.7 cell lines were maintained in Dulbecco's modified Eagle's medium (DMEM) supplemented with 10% fetal bovine serum and penicillin and streptomycin in the concentrations noted above.

Transfection of J558L cells was performed by electroporation, after the method of Potter H. et al. Proc. Natl. Acad. Sci. USA 81:7161–7165 (1984). Twenty micrograms of linearized (pIgTElN-mIP10) or (MoLTR-mIP10-SV40 I/pA) DNA and 1 μg of linearized pSV7Neo (Murphy, W. et al., Proc. Natl. Acad. Sci. USA 83:2939–2943 (1986)) (which contains a neomycin resistance gene), was used per transfection of 5×10⁶ cells. After 48 hr in RPMI medium, cells were centrifuged and resuspended in selective medium containing 0.8 mg/ml of G418 (as calculated for 100% antibiotic activity; Geneticin, GIBCO) and plated serial dilutions into 288 6.4 mm diameter wells to clone by limiting dilution individual colonies. G418 resistant cells from single wells were expanded and single cell clones were obtained by a second round of limiting dilution in selective medium. Transfection of K485 cells was performed by electroporation using 30 μg of linearized vector MoLTR-mIP-10-SV40 I/pA and 15 microgram linearized pSV7Neo DNA 100 mm plate containing 6×10⁵ cells. Twenty-four hours after transfection, cells were split 1:3 in DMEM; G418 at a concentration of 0.4 mg/ml was added after an additional 24 hr. Individual G418-resistant colonies were picked after 10–12 days and then to insure clonality single cell clones were then isolated by limiting dilution in selective medium. In vitro doubling times were determined by serial cell counts at 12 hr intervals over a 48 hr period.

3. Protein Purification and Antibody Preparation

Recombinant mIP-10 was expressed in the *E. coli* strain M15 using the Qiaexpress vector pQE12 which attaches a six histidine carboxy-terminal tag (Qiagen). IP-10 was purified to apparent homogeneity by sedimentation of inclusion bodies through sucrose, affinity chromatography on nickel agarose (Qiagen), and FPLC on the cation exchange resin Mono-S (Pharmacia). The concentration of purified protein was determined using a modified Bradford assay and IgG as the known standard.

For immunizations, IP-10 was purified as above, except that the eluent from the nickel-agarose chromatography column was separated on a denaturing SDS-polyacrylamide gel. The region of the gel containing IP-10 was then emulsified with complete Fruend's adjuvant for the primary immunization and with incomplete Fruend's adjuvant for subsequent immunizations. Approximately 200 micrograms of IP-10 was injected subcutaneously into each of three, eight week old, female New Zealand white rabbits. The rabbits were boosted twice, at one month intervals, with 100 micrograms of IP-10 per rabbit. Ten days after the second boost, the three rabbits were bled and serum was isolated and pooled for further studies.

4. ELISA Quantitation of IP-10

The approximate concentration of IP-10 in the conditioned medium of the stably transfected cell lines was determined by comparing the ELISA value to that of a standard curve obtained using the purified IP-10. Conditioned medium was collected for 24 hours from 2×10⁶ cells/ml and 100 microliters was then adsorbed in duplicate to microtiter wells (Falcon 3911 Micro Test III) for 4 hours. Nonspecific binding sites were blocked for 2 hours at room temperature with 200 microliters/well of a phosphate buffered saline solution containing 2% goat serum and 2% bovine serum albumin (blocking solution). This was followed by 100 microliters/well of anti-IP-10 antiserum at a 1:1000 dilution in blocking solution for 2 hours at room temperature. The plates were then washed 4 times with water, incubated for 1 hours at room temperature with a 1:10,000 dilution of an alkaline phosphatase conjugated goat anti-rabbit IgG (Jackson ImmunoResearch), washed 4 more times with water and treated with 100 microliters/well of the substrate p-Nitrophenyl phosphate in 1× (one ×) diethanolamine (Pierce). The $v_{max}$ mOD$_{405}$/min was measured on a Molecular Devives $v_{max}$ kinetic micro plate reader.

5. Animal Studies

BALB/c Swiss and nu/nu Swiss and nu/nu Balb/c mice were obtained from Jackson Laboratory (Bar Harbor, ME) and Taconic Farms (Germantown, N.Y.), respectively. Tumor cell injections were carried out using freshly prepared suspensions at a concentration 1×10⁷cells/mi. The total number of tumor cells injected per animal was 2×10⁶except for mixed tumor transplantation experiments (see below). All injections were performed subcutaneously in the right lower abdominal quadrant via 25-gauge needles on plastic 1 cc syringes. For experiments involving antibody administration, polyclonal rabbit IgG was purified from rabbit serum by protein A Sepharose affinity chromatography and can be given as a 0.5 cc intraperitoneal injection at weekly intervals for a period of 4 weeks.

6. The Mixed Tumor Transplantation Assay

Transfected IP-10 producing cells were mixed with non-expressing tumor cells using 2 ×106 cells of each type. The mix was injected subcutaneously in a volume of 0.4 ml (according to the method described above) into syngeneic mice. Animals injected with IP-10 non-expressing tumor cells alone served as controls.

7. DNA Preparation

DNA was extracted from cell pellets or tumors according to a protocol modified from Davis R. W. et al., Meth. Enzymol. 65:404–411 (1980), using a single phenolchloroform extraction prior to ethanol precipitation. The nucleic acid pellet was resuspended in 10 mM Tris, 1 mM EDTA at an approximate concentration of 1 μg/μl.

8. DNA Blots

DNA blots to detect the presence or absence of the transfected IP-10 gene in tumors can be performed according to the procedure of Southern (1975), using 10 μg of cell line or tumor DNA per lane, and can be hybridized to a mIP10 cDNA probe radiolabeled with α-[$^{32}$P]dCTP using the random hexamer priming method (Feinberg, A. P. et al., Anal. Biochem. 132:6–13 (1983)).

9. RNA blots

RNA was isolated from cell lines or tumor tissue by the procedure of Chirgwin, J. M. et al., Biochemistry 18: 5294–5299 (1979) using the CsCl sedimentation gradient modification. RNA was dissolved in sterile distilled water and the yield determined by UV absorption at 260 nm. RNA was fractionated on a 1.2% agarose gel containing 0.2M formaldehyde and then transferred to gene screen (Dupont) and hybridized with $^{32}$P-labeled mIP-10 cDNA or the SV40 I/pA gene fragment derived from the above mentioned expression vectors 10. Histologic Evaluation Tissue at the site of tumor cell inoculation was fixed in Optimal Fix (American Histology Reagent Co.), paraffin-embedded, and stained with Giemsa.

III. THERAPEUTIC ADMINISTRATION OF IP-10 POLYPEPTIDE.

With the availability of the cloned gene, the substantially pure IP-10 polypeptide can be produced in quantity using standard techniques (Scopes, R. *Protein Purification: Principles and Practice* 1982 Springer-Verlag, N.Y.). Thus, another aspect of the invention is a pharmaceutical comprising the IP-10 polypeptide together with an acceptable diluent, carrier or excipient and/or in unit dosage form. Conventional pharmaceutical practice may be employed to provide suitable formulations or compositions to administer the polypeptide to patients with a neoplasia.

A substantially pure preparation of a polypeptide is a preparation which is substantially free (e.g., to the extent required for formulating IP-10 into a therapeutic composition) of the proteins with which it naturally occurs in a cell.

Fragments or analogs of the IP-10 protein may also be administered to a patient with a neoplasia in the manner described above. Fragments or analogs which are useful for this purpose include those which are described above and are useful for the treatment of a patient with a neoplasia. Fragments and analogs which will be useful for the therapeutic treatment of patients with a neoplasia are determined using the assays provided in the examples, below, among others.

The IP-10 polypeptide may also be administered to a patient with a neoplasia in the form of a fusion protein consisting of a IP-10 polypeptide, fused to the a ligand or receptor protein, or a fragment thereof, which is sufficient to bind a receptor or a receptor ligand on the cell to which IP-10 may desirably be delivered.

The IP-10 ligand fusion polypeptide may be generated using standard techniques of molecular biology to generate fusions encoded from a suitable vector (Sambrook et al., *Molecular Cloning: A Laboratory Manual*, Cold Spring Harbor Laboratory Press, New York (1989)). The usefulness of such gene fusion constructs may be determined using the methods described above in the experimental methods and below in the examples, among others. The invention includes administering either type of fusion polypeptide alone or in a pharmaceutically acceptable carrier.

Thus, the formulations of this invention can be applied for example by parenteral administration, intravenous, subcutaneus, intramuscular, intracranial, intraorbital, opthalmic, intraventricular, intracapsular, intraspinal, intracisternal, intraperitoneal, intranasal, aerosol, or oral administration.

Therapeutic Formulations may be in the form of liquid solutions or suspensions; for oral administration, formulations may be in the form of tablets or capsules; and for intranasal formulations, in the form of powders, nasal drops, or aerosols.

Methods well known in the art for making formulations are to be found in, for example, "Remington's Pharmaceutical Sciences". Formulations for parenteral administration may, for example, contain excipients sterile water or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of present factors. Other potentially useful parenteral delivery systems for the factors include ethylene-vinyl acetate copolymer particals, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally.

IV. THERAPEUTIC ADMINISTRATION OF ID-10 IN A VIRAL VECTOR

The following example illustrates, but does not limit the invention.

Retroviral vectors, or other viral vectors with the appropriate tropisms for cells useful for therapeutic delivery, may be used as a gene transfer delivery system for the IL-10 polypeptide. Numerous vectors useful for this purpose are generally known have been described (Miller, Human Gene Therapy p. 15–14 (1990); Friedman, Science 244:1275–1281 (1989); Eglitis and Anderson, BioTechniques 6:608–614 (1988); Tolstoshev and Anderson, Current Opinion in Biotechnology 55–61 (1990); Sharp, The Lancet 337:1277–1278 (1991); Cornetta et al., Nucleic Acid Research and Molecular Biology 36: 311–322 (1987); Anderson, Science 226:401–409 (1984); Moen, Blood Cells 17:407–416 (1991); and Miller and Rosman, Biotechniques 7:980–990 (1989)). Retroviral vectors are particularly well developed and have been used in a clinical setting (Rosenberg, et al N. Engl. J. Med 323:370 (1990)).

The retroviral constructs, packaging cell lines and delivery systems which may be useful for this purpose include, but are not limited to, one, or a combination of, the following: Moloney murine leukemia viral vector types; self inactivating vectors; double copy vectors; selection marker vectors; and suicide mechanism vectors. The Moloney murine leukemia retroviral system of IP-10 delivery is particularly useful since it targets delivery of the IP-10 protein to the hematopoietic cells which may be used for autologous of non-antologous therapy.

Fragments or derivatives of the IP-10 polypeptide may also be administered by retroviral gene transfer therapy or another suitable viral vector system. Fragments or derivatives are defined as described above. Useful fragments or derivatives of IP-10 may be administered by inserting the nucleic acids encoding these fragments or derivatives in place of the complete IP-10 encoding gene in a gene therapy vector, as described above. Such constructs may be tested using the methods for testing the effects of IP-10 on viral infectivity described above, among others.

Retroviral delivery of IP-10 or other forms of gene transfer are particularly appropriate for neoplasms of the immune system, as removal, treatment, and reimplantation of hematopoietic cells is a matter of course for the treatment of these neoplasms. Standard techniques for the delivery of gene therapy vectors may be used to transfect stem cells. Such transfection may result in IP-10 synthesizing cells useful in lowering the recurrence rate of the neoplasia in the patient.

V. NON VIRAL METHODS FOR THE THERAPEUTIC DELIVERY OF NUCLEIC ACID ENCODING IP-10

Nucleic acid encoding IP-10 or a fragment thereof, under the regulation of the appropriate promotor, and including the appropriate sequences required for insertion into genomic DNA of the patient, or autonomous replication, may be administered to the patient using the following gene transfer techniques: microinjection (Wolff et al., Science 247:1465 (1990)); calcium phosphate transfer (Graham and Van der Eb, Virology 52:456 (1973); Wigler et al., Cell 14:725 (1978); Felgner et al., Proc. Natl. Acad. Sci. USA 84:7413 (1987)); lipofection (Felgner et al., Proc. Natl. Acad. Sci. USA 84:7413 (1987); Ono et al., Neuroscience Lett 117:259 (1990); Brigham et al., Am. J. Med. Sci. 298:278 (1989); Staubinger and Papahadjopoulos, Meth. Enz. 101:512 (1983)); asialorosonucoid-polylysine conjugation (Wu and Wu, J. Biol. Chem. 263:14621 (1988); Wu et al., J. Biol. Chem. 264:16985 (1989)); and electroporation (Neumnn et al., EMBO J. 7:841 (1980)). These references are hereby incorporated by reference.

VI. EXAMPLE 1

Prevention of Tumor Formation in Mice Using IP-10

Two expression vectors (depicted in FIG. 2) were constructed bearing either the Molney virus promoter/LTR or an immunoglobulin promoter/enhancer driving a cDNA encoding IP-10 and a segment of the SV40 T antigen gene containing a splice linkage and polyadenylation addition site. These were transfected in the several tumor cell lines (See Tepper et al., Cell 57:503–512, 1989).

The relative expression of IP-10 by the transfected cells was determined using an ELISA immunoassay (FIG. 3 (a) and 3(b)) and the high-level-of-expression lines derived from mouse plasmacytoma (J558L) cells and mammary adenocarcinoma (K485) cells were selected for tumorigenesis study.

Specifically shown in FIGS. 3(a) and 3(b) are quantitation of secreted IP-10 immunoreactivity from IP-10 producing cell lines using an ELISA assay. FIG. 3(a) depicts standard curve on purified recombinant IP-10 produced in *E. Coli*. The recombinant murine IP-10 was expressed in *E. Coli* using the Qiaexpress vector pQE12 which attaches a six histidine carboxy-terminal tag. IP-10 was then purified to apparent homogeneity by sedimentation of inclusion bodies through sucrose, affinity chromatography on nickel agarose, and FPLC on the cation exchange resin Mono-S. The concentration of the purified protein was determined using a modified bradford assay using IgG as the known standard.

FIG. 3(b) depicts the ELISA determination IP10 secreted into the medium from $2\times10^6$ cells over a 24 hour period.

Approximately $2\times10^6$ cells were injected subcutaneously into the right lower abdominal quadrant of appropriate inbred mice (BALB/C for the J558L cells, FVB for K485 cells) and the mice were autopsied and the tumors extirpated and weighed 10–14 days later. As shown in Table 1, the IP-10 producing J558L tumors cells that grew well in culture, failed to grow when injected in to the host. Non-IP-10-producing host cells grew well. The anti-tumor effect did not require that IP-10 be produced by all tumor cells and this was shown (Table 2) by mixing producer and non-producer cells and transplanting them to host mice as described above. Thus, the effect is non-cell autonomous. That the effect is not restricted to a single tumor type was shown by demonstrating its efficacy using IP-10-producing carcinoma cells (K485, mammary adenocarcinoma). As shown in Table 3, the producing cells also fail to form tumors.

TABLE 1

Tumorigenicity of J558L Cells and Transfectants in Syngeneic Balb/c and Nude Mice

| | Tumor occured* | |
|---|---|---|
| J558L Transfected with | Balb/c | nu/nu (Balb/c, Swiss) |
| None | 19/19 | 7/8 |
| neo$^R$ alone | 4/5 | 5/5 |
| MoLTR-IP10 | 0/14 | 12/16 |
| Ig-IP10 | 2/14 | 12/16 |

*Mice were autopsied 10–14 days after $2 \times 10^6$ cells were injected subcutaneously into the right lower abdominal quadrant. The weight of the extirpated tumor or residual scar was determined and a tumor mass was considered positive if it weight $\geq 0.5$ grams. This table is a compilation of 7 different experiments.

TABLE 2

IP-10's Effect in Mixed Tumor Cell Transplantation

| Cell | Tumor occured |
|---|---|
| J558L-neo$^R$ alone | 4/5 |
| 1:1 mix of J558L-neo$^R$ and J558L transfected with | |
| MoLTR-IP10 | 0/5 |
| Ig-IP10 | 1/5 |

Mice were autopsied 14 days after $2 \times 10^6$ of each cell type was injected subcutaneously into the right lower abdominal quadrant. Tumors were extirpated and considered positive if they weight 0.5 grams.

TABLE 3

Effect of IP-10 on the Tumorigenicity of Mammary Adenocarcinoma Cells in Syngeneic mice

| Cell Line | Tumor occured* |
|---|---|
| K485-neo$^R$ | 3/4 |
| K485-IP10 | 0/5 |

*Mice were autopsied 28 days after $2 \times 10^6$ cells were injected subcutaneously into the right lower abdominal quadrant. Tumors were associated with a tense bloody malignant ascites.

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
( A ) LENGTH: 361
( B ) TYPE: nucleic acid
( C ) STRANDEDNESS: single
( D ) TOPOLOGY: linear ( x i ) SEQUENCE DESCRIPTION: SEQ ID NO: 1:

```
CATCCCGAGC  CAACCTTCCG  GAAGCCTCCC  CATCAGCACC  ATG  AAC  CCA  AGT  GCT           55
                                                Met  Asn  Pro  Ser  Ala
                                                 1                    5

GCC  GTC  ATT  TTC  TGC  CTC  ATC  CTG  CTG  GGT  CTG  AGT  GGG  ACT  CAA  GGG   103
Ala  Val  Ile  Phe  Cys  Leu  Ile  Leu  Leu  Gly  Leu  Ser  Gly  Thr  Gln  Gly
               10                         15                         20

ATC  CCT  CTC  GCA  AGG  ACG  GTC  CGC  TGC  AAC  TGC  ATC  CAT  ATC  GAT  GAC   151
Ile  Pro  Leu  Ala  Arg  Thr  Val  Arg  Cys  Asn  Cys  Ile  His  Ile  Asp  Asp
               25                         30                         35

GGG  CCA  GTG  AGA  ATG  AGG  GCC  ATA  GGG  AAG  CTT  GAA  ATC  ATC  CCT  GCG   199
Gly  Pro  Val  Arg  Met  Arg  Ala  Ile  Gly  Lys  Leu  Glu  Ile  Ile  Pro  Ala
               40                         45                         50

AGC  CTA  TCC  TGC  CCA  CGT  GTT  GAG  ATC  ATT  GCC  ACG  ATG  AAA  AAG  AAT   247
Ser  Leu  Ser  Cys  Pro  Arg  Val  Glu  Ile  Ile  Ala  Thr  Met  Lys  Lys  Asn
          55                         60                         65

GAT  GAG  CAG  AGA  TGT  CTG  AAT  CCG  GAA  TCT  AAG  ACC  ATC  AAG  AAT  TTA   295
Asp  Glu  Gln  Arg  Cys  Leu  Asn  Pro  Glu  Ser  Lys  Thr  Ile  Lys  Asn  Leu
 70                         75                         80                   85

ATG  AAA  GCG  TTT  AGC  CAA  AAA  AGG  TCT  AAA  AGG  GCT  CCT  TAACTGGAGA      344
Met  Lys  Ala  Phe  Ser  Gln  Lys  Arg  Ser  Lys  Arg  Ala  Pro
               90                         95

GAAGCCACGC  ACACACC                                                              361
```

( 2 ) INFORMATION FOR SEQ ID NO: 2:

( i ) SEQUENCE CHARACTERISTICS:
( A ) LENGTH: 17
( B ) TYPE: nucleic acid
( C ) STRANDEDNESS: single
( D ) TOPOLOGY: linear ( x i ) SEQUENCE DESCRIPTION: SEQ ID NO: 2:

```
AAGCGCTTCA  TCCACCG                                                               17
```

( 2 ) INFORMATION FOR SEQ ID NO: 3:

( i ) SEQUENCE CHARACTERISTICS:
( A ) LENGTH: 17
( B ) TYPE: nucleic acid
( C ) STRANDEDNESS: single
( D ) TOPOLOGY: linear ( x i ) SEQUENCE DESCRIPTION: SEQ ID NO: 3:

```
GCGTGGCTTC  TCTCCAG                                                               17
```

Other embodiments are within the following claims.

What is claimed is:

1. A method for inhibiting a neoplasm in a mammal, said method comprising administering to said mammal a neoplasm inhibiting amount of IP-10 polypeptide, wherein said IP10 polypeptide has the sequence of a naturally-occurring human or mouse IP-10 polypeptide, wherein said mammal is selected from the group consisting of a human and a mouse, and wherein said neoplasm is selected from the group consisting of a carcinoma, a leukemia, and a lymphoma.

2. The method of claim 1 wherein said neoplasm is a leukemia or lymphoma.

3. The method of claim 1 wherein said neoplasm is a carcinoma.

4. The method of claim 1 wherein said neoplasm is a mammary adenocarcinoma.

5. The method of claim 1, wherein said IP-10 polypeptide is in a pharmaceutically acceptable carrier.

* * * * *